(12) United States Patent
Gysling (10) Patent No.: US 7,059,171 B2
(45) Date of Patent: *Jun. 13, 2006

(54) FLUID DENSITY MEASUREMENT USING ACOUSTIC PRESSURES FOR INDUSTRIAL SENSING APPLICATIONS

(75) Inventor: Daniel L. Gysling, Glastonbury, CT (US)

(73) Assignee: Weatherford/Lamb, Inc., Houston, TX (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/011,605

(22) Filed: Nov. 9, 2001

(65) Prior Publication Data

US 2003/0089161 A1    May 15, 2003

Related U.S. Application Data

(63) Continuation-in-part of application No. 10/010,183, filed on Nov. 7, 2001, now Pat. No. 6,971,259.

(51) Int. Cl.
*G01N 9/36* (2006.01)

(52) U.S. Cl. .................................. 73/32 A; 73/24.05

(58) Field of Classification Search ................ 73/32 A, 73/32 R, 24.01, 24.05, 24.06, 61.79, 61.41, 73/61.47, 61.49, 597, 643, 655, 656, 657
See application file for complete search history.

(56) References Cited

U.S. PATENT DOCUMENTS

| 4,445,389 A | * | 5/1984 | Potzick et al. | ........... 73/861.27 |
| 4,677,305 A | * | 6/1987 | Ellinger | .................... 73/290 V |
| 5,359,897 A | * | 11/1994 | Hamstead et al. | ............ 73/597 |
| 5,719,329 A | * | 2/1998 | Jepson et al. | ............... 73/61.49 |

(Continued)

Primary Examiner—Helen Kwok
(74) Attorney, Agent, or Firm—Patterson & Sheridan, LLP (57) ABSTRACT

The density of at least one fluid in a pipe 12 is determined using a pair of effective sound speeds $a_{1\mathit{eff}}$ and $a_{2\mathit{eff}}$ of the fluid/pipe system. The pair of effective system sound speed measurements are taken at two sensing regions $X_1$, $X_2$ along the pipe wherein each of the sensing regions comprises a different system cross sectional compliance. The pair of effective system sound speeds $a_{1\mathit{eff}}$ and $a_{2\mathit{eff}}$ are provided to signal processing logic 60, which determines the density of the fluid 13 flowing in the pipe 12. The effective system sound speeds $a_{1\mathit{eff}}$ and $a_{2\mathit{eff}}$ may be provided by a pair of sound speed meters positioned at sensing regions $X_1$, $X_2$ wherein the sound speed meters utilize a spatial array of acoustic pressure sensors placed at predetermined axial locations along the pipe 12. The acoustic pressure sensors provide acoustic pressure signals which are utilized to determine the effective system speed of sound $a_{1\mathit{eff}}$ and $a_{2\mathit{eff}}$ of the fluid (or mixture)/pipe system. One technique uses acoustic spatial array signal processing techniques with the direction of propagation of the acoustic signals along the longitudinal axis of the pipe 12. However, numerous spatial array-processing techniques may be employed to determine the effective system speed of sounds $a_{1\mathit{eff}}$ and $a_{2\mathit{eff}}$. The effective system sound speeds $a_{1\mathit{eff}}$ and $a_{2\mathit{eff}}$ measured utilize one-dimensional planar acoustic waves that are lower in frequency (and longer wavelength) signals than those used for ultrasonic flow meters, and thus incorporates pipe compliance with fluid compliance and further is more tolerant to inhomogeneities in the flow. In addition, no external source is required and thus may operate using passive listening. The invention will work with arbitrary sound speed meter spacing and with as few as two sound speed meters. The density meter may also be combined with an instrument, an opto-electronic converter and a controller in an industrial process control system.

20 Claims, 5 Drawing Sheets

U.S. PATENT DOCUMENTS

| | | | |
|---|---|---|---|
| 5,835,884 A * | 11/1998 | Brown | 73/861.02 |
| 6,202,494 B1 * | 3/2001 | Ricbel et al. | 73/861.29 |
| 6,349,599 B1 * | 2/2002 | Lynnworth et al. | 73/644 |
| 6,354,147 B1 * | 3/2002 | Gysling et al. | 73/61.79 |
| 6,435,030 B1 * | 8/2002 | Gysling et al. | 73/587 |
| 6,442,996 B1 * | 9/2002 | Thurston et al. | 73/24.01 |
| 6,446,494 B1 * | 9/2002 | Hastings et al. | 73/54.41 |
| 6,450,037 B1 * | 9/2002 | McGuinn et al. | 73/705 |
| 6,502,465 B1 * | 1/2003 | Vedapuri et al. | 73/861.04 |
| 6,732,575 B1 * | 5/2004 | Gysling et al. | 73/61.79 |

* cited by examiner

Figure 9

FLUID DENSITY MEASUREMENT USING ACOUSTIC PRESSURES FOR INDUSTRIAL SENSING APPLICATIONS

CROSS REFERENCES TO RELATED APPLICATIONS

This application is a continuation-in-part of commonly owned co-pending U.S. patent application, Ser. No. 10/010,183, entitled "Fluid Density Measurement in Pipes Using Acoustic Pressures", filed Nov. 7, 2001 now U.S. Pat. No. 6,971,259. This application contains subject matter related to that disclosed in commonly owned U.S. patent applications, Ser. No. 10/007,749, entitled "Fluid Parameter Measurement for Industrial Sensing Applications Using Acoustic Pressures", filed Nov. 8,2001, Ser. No. 10/007,736. entitled "Flow Rate Measurement for Industrial Sensing Applications Using Unsteady Pressures", filed Nov. 8, 2001, Ser. No. 09/344,070, entitled "Measurement of Propagating Acoustic Waves in Compliant Pipes", filed Jun. 25, 1999, Ser. No. 09/344,069, entitled "Displacement Based Pressure Sensor Measuring Unsteady Pressure in a Pipe", filed Jun. 25, 1999, and Ser. No. 09/344,093, entitled "Non-Intrusive Fiber Optic Pressure Sensor for Measuring Unsteady Pressures within a Pipe", filed Jun. 25, 1999, all of which are incorporated herein by reference.

TECHNICAL FIELD

This invention relates to fluid parameter measurement in pipes and more particularly to measuring speed of sound and density of fluids in pipes using acoustic pressures for use in industrial sensing applications. The measurement exploits the interaction between pipe flexibility, speed of sound propagation, and density of the fluid within a conduit.

BACKGROUND ART

An industrial process sensor is typically a transducer that responds to a measurand with a sensing element and converts the variable to a standardized transmission signal, e.g., an electrical or optical signal, that is a function of the measurand. Industrial process sensors utilize transducers that include flow measurements of an industrial process such as that derived from slurries, liquids, vapors and gasses in refinery, chemical, paper, pulp, petroleum, gas, pharmaceutical, food, mining, minerals and other fluid processing plants. Industrial process sensors are often placed in or near the process fluids, or in field applications. Often, these field applications are subject to harsh and varying environmental conditions that provide challenges for designers of such sensors. Flow measurement is one of the largest segments of the industrial sensing and instrumentation market. Industries in which flow measurements are prevalent includes petroleum, chemical, pulp, paper, food, and mining and minerals.

Typical electronic, or other, transducers of the prior art often cannot be placed in industrial process environments due to sensitivity to electromagnetic interference, radiation, heat, corrosion, fire, explosion or other environmental factors. It is for these reasons that fiber optic based sensors are being incorporated into industrial process control environments in increasing number.

Further, it is known that the speed of sound $a_{mix}$ of fluids in pipes may be used to determine various parameters of the fluid, such as is described in U.S. Pat. No. 4,080,837, entitled "Sonic Measurement of Flow Rate and Water Content of Oil-Water Streams", to Alexander et al., U.S. Pat. No. 5,115,670, entitled "Measurement of Fluid Properties of Two-Phase Fluids Using an Ultrasonic Meter", to Shen, and U.S. Pat. No. 4,114,439, entitled "Apparatus for Ultrasonically Measuring Physical Parameters of Flowing Media", to Fick. Such techniques have a pair of acoustic transmitters/receivers (transceivers) that generate a sound signal and measure the time it takes for the sound signal to travel between the transceivers. This is also known as a "sing-around" or "transit time" method. However, such techniques require precise control of the acoustic source and are costly and/or complex to implement in electronics.

Also, these techniques use ultrasonic acoustic signals as the sound signal measured, which are high frequency, short wavelength signals (i.e., wavelengths that are short compared to the diameter of the pipe). Typical ultrasonic devices operate near 200 k Hz, which corresponds to a wavelength of about 0.3 inches in water. In general, to allow for signal propagation through the fluid in an unimpeded and thus interpretable manner, the fluid should be homogeneous down to length scales of several times smaller than the acoustic signal wavelength. Thus, the criterion for homogeneity of the fluid becomes increasingly more strict with shorter wavelength signals. Consequently, inhomogeneities in the fluid, such as bubbles, gas, dirt, sand, slugs, stratification, globules of liquid, and the like, will reflect or scatter the transmitted ultrasonic signal. Such reflection and scattering inhibit the ability of the instrument to determine the propagation velocity. For this reason, the application of ultrasonic flowmeters has been limited primarily to well mixed flows.

Gamma-densitometers are widely used in the art for performing density measurements of fluids within pipes. These devices utilize a nuclear source to expose the fluids to a gamma radiation beam and measure density based on gamma beam absorption. The primary drawbacks of this type of density meter are the environmental and safety issues associated with the nuclear sources.

Another prior art method of determining the density of a fluid within a pipe is through the use of Corriolis meter. A Corriolis meter measures mass flow and density as the primary measurements by tracking the natural frequency of a vibrating pipe filled with the fluid. These devices require a vibration source, among other elements, which make Corriolis meters mechanically complex, and relatively expensive to install and maintain.

SUMMARY OF THE INVENTION

Objects of the present invention include provision of a system for measuring the density of fluids in pipes in industrial sensing applications.

According to the present invention, an apparatus for measuring the density of at least one fluid in a pipe, comprising at least two sound speed meters, disposed at different sensing regions along the pipe, and each measuring an acoustic pressure within the pipe at a corresponding axial location, each of the sound speed meters providing a system effective sound speed signal indicative of the propagation velocity of a one-dimensional acoustic pressure wave traveling along the pipe at the sensing region of a corresponding one of the sound speed meters and a signal processor, responsive to the sound speed signals, which provides a signal indicative of the density of the fluid in the pipe.

According further to the present invention, the cross sectional compliance of the two sensing regions is substantially different from one another. According still further to the present invention, the compliance of the pipe is different in each of the two sensing regions. In still further accord to the present invention, the cross sectional geometry of the pipe is of a non-circular geometry in one of the two sensing regions.

According still further to the present invention, the sound speed meters are fiber optic based sound speed meters. Still further in accord to the present invention, the sound speed meters are isolated from an outside environment by a concentric shell. Further according to the present invention, the shell comprises an evacuated space, or is filled with a fluid of known acoustic impedance.

The present invention provides a significant improvement over the prior art by providing a measurement of the density $\rho_{mix}$ of a mixture of one or more fluids within a pipe (where a fluid is defined as a liquid or a gas) by using an axial array of sound speed meters positioned along the pipe. An explicit acoustic noise source is not required, as the background acoustic noises within the pipe (or fluid therein) will likely provide sufficient excitation to enable characterization of the speed of sound of the mixture by merely passive acoustic listening.

The invention works with acoustic signals having lower frequencies (and thus longer wavelengths) than those used for ultrasonic meters, such as below about 20 k Hz (depending on pipe diameter). As such, the invention is more tolerant to the introduction of gas, sand, slugs, or other inhomogeneities in the flow.

The present invention allows the density to be determined in a pipe independent of pipe orientation, i.e., vertical, horizontal, or any orientation therebetween. Also, the invention does not require any disruption to the flow within the pipe (e.g., an orifice or venturi). Furthermore, if harsh environment fiber optic sound speed meters are used to obtain the effective system sound speed measurements, such meters eliminate the need for any electronic components down-hole, thereby improving reliability of the measurement.

Also, a strain gauge (optical, electrical, etc.) based sound speed meter that measures hoop strain on the pipe may be used to measure the ac pressure. Fiber optic wrapped sensors may be used as optical strain gauges to provide circumferentially averaged pressure. Thus, the present invention provides non-intrusive measurements of the density of the fluid, which enables real time monitoring and optimization for oil and gas exploration and production.

The density meter may also be combined with an instrument, an opto-electronic converter and a controller in an industrial process control system.

The foregoing and other objects, features and advantages of the present invention will become more apparent in light of the following detailed description of exemplary embodiments thereof.

BEST MODE FOR CARRYING OUT THE INVENTION

Figure 1:
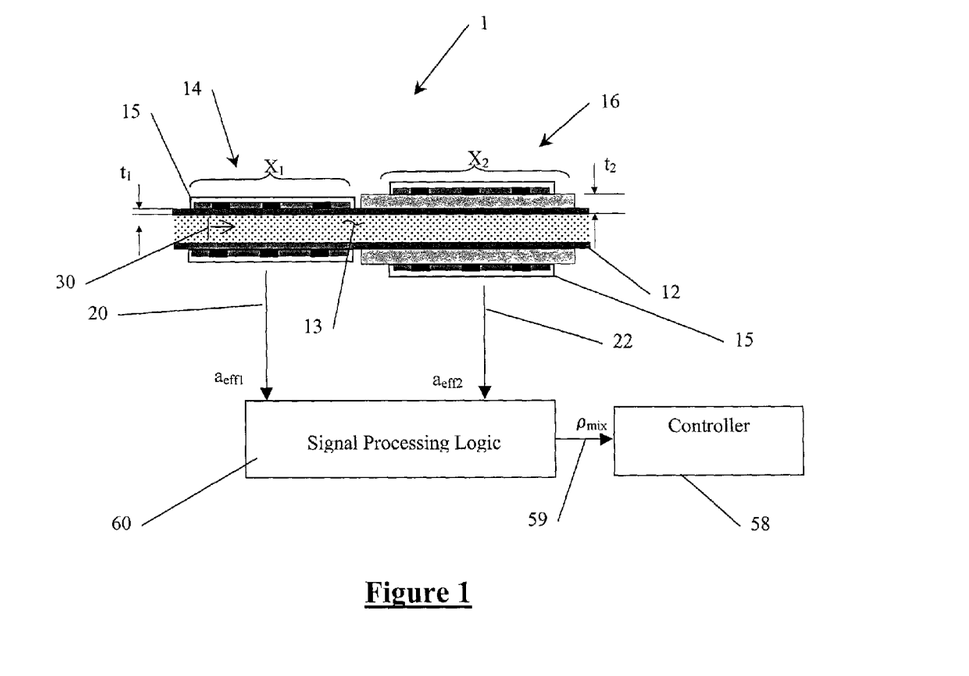
FIG. 1 is a schematic block diagram of a density meter system, in accordance with the present invention.

Density meter 1 in FIG. 1 using a pair of sound speed meters 14,16 placed at axial locations, or sensing regions, X1, X2 along the pipe 12, measures the density of at least one fluid in a pipe 12. The sound speed meters 14,16 provide the effective speed of sound $a_{1eff}$ and $a_{2eff}$ of the fluid/pipe system on lines 20,22 which are provided to signal processing logic 60 which determines the density of the fluid (or mixture) in the pipe 12 using relationships between the compliance of the pipe and various fluid parameters as will be more fully described herein below. Numerous sensing and processing techniques may be employed to determined the speed of sound $a_{mix}$ of fluid and fluid/pipe system $a_{eff}$, such as those disclosed in commonly owned copending U.S. patent application Ser. No. 09/344,094, entitled Fluid Parameter Measurement in Pipes Using Acoustic Pressures, the disclosure of which is incorporated herein by reference in its entirety.

Also, some or all of the functions within the logic 60 may be implemented in software (using a microprocessor or computer) and/or firmware, or may be implemented using analog and/or digital hardware, having sufficient memory, interfaces, and capacity to perform the functions described herein.

The effective speeds of sound $a_{1eff}$ and $a_{2eff}$ are provided to logic 60 wherein the logic calculates the density of the fluid by from the difference in the effective sound speeds as will be more fully described herein below. Sound speed meters 14, 16 utilize acoustic pressure signals that, as measured, are lower frequency (and longer wavelength) signals than those used for ultrasonic flow meters of the prior art, and thus the current invention is more tolerant to inhomogeneities in the flow. In addition, the present invention differs from prior art fluid parameter measurement devices in that the present invention incorporates the compliance of the pipe to determine the effective speed of sound of the pipe/fluid system. The typical frequency range for acoustic pressure signals of the present invention is from about 10 Hz to about 10,000 Hz. The acoustic pressure signals are generated within the fluid of the pipe 12 by a variety of non-discrete sources such as remote machinery, pumps, valves, elbows, as well as the fluid flow itself. It is this last source, the fluid flowing within the pipe, that is a generic source of acoustic noise that assures a minimum level of acoustics for any fluid piping systems for which the present invention takes unique advantage. The flow generated acoustics increase with mean flow velocity and the overall noise levels (acoustic pressure levels) are a function of the generating mechanism and the damping mechanism. Experience indicates that pipe systems typically have sufficient ambient noise levels of 100 to 180 dbA.

No external discrete noise source is required within the present invention and thus may operate using passive listening. It is within the scope of the present that the sound meter or sensor 14, 16 spacing may be known or arbitrary and that as few as two sensors are required if certain information is known about the acoustic properties of the system as will be more fully described herein below.

It is an important aspect of the present invention that one-dimensional, planar compression waves 30 propagating within a fluid contained within a conduit 12 exert an unsteady internal pressure loading on the conduit. The degree to which the conduit displaces as a result of the unsteady pressure loading influences the speed of propagation of the compression wave 30 within the context of the fluid/pipe system. For a given fluid, the more compliant the conduit, the greater the reduction of the propagation velocity of the compression wave. Also, for a given pipe stiffness, the denser the fluid and the higher the infinite volume sound speed, the greater the reduction in the speed of sound due to the pipe flexibility or compliance.

The relationship among the infinite domain speed of sound ($a_{mix\infty}$) and density ($\rho_{mix}$) of a fluid; the elastic modulus of the pipe (E), thickness of the pipe (t), and radius of a vacuum-backed cylindrical conduit (R), the effective propagation velocity ($a_{eff}$) for a one dimensional compression wave is given by the following expression:

$$a_{eff} = \cfrac{1}{\sqrt{\cfrac{1}{a_{mix\infty}^2} + \rho_{mix}\cfrac{2R}{Et}}} \quad \text{(eq 1)}$$

Figure 2:
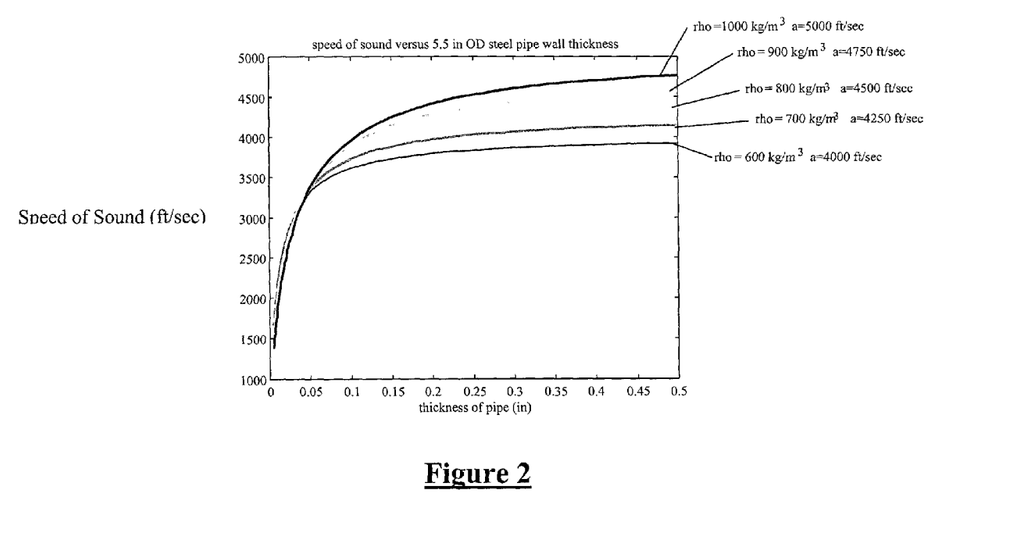
FIG. 2 is a graphical representation of the effective system speed of sound of a fluid/pipe for various pipe wall thicknesses, in accordance with the present invention.

FIG. 2 shows the effective propagation velocity, or effective system sound speed for a specific example of the density meter 1 of FIG. 1 in accordance with the present invention. In this particular embodiment the effective system sound speed is shown for a fluid contained in a vacuum-backed, cylindrical steel conduit with acoustic propagation velocities and density representative of hydrocarbon liquid and water mixtures as typically found in the oil and gas industry. FIG. 2 shows the effect of varying the compliance of the pipe/fluid system by changing the wall thickness of a 5.50 inch OD steel pipe from some theoretical minimum value to a thickness of 0.5 inches for five different fluids having densities from 600 to 1000 kg/m³. As shown in FIG. 2, varying the thickness of the pipe has a significant effect on the effective speed of sound of the fluid/pipe system. For simplicity sake, the present invention is described with regard to particular embodiments comprising vacuum-backed conduits having sufficiently low frequencies (compared to breathing mode and resonant frequencies) that the pertinent dynamical response is captured by the static compliance of the conduit. The conduit may be vacuum backed by a concentric shell 15 (FIG. 1) or other suitable structure to isolate the sensing regions $X_1$, $X_2$ from the outside environment. In alternative embodiments the sensing regions $X_1$, $X_2$ may be isolated within the concentric shell 15 by a known fluid or air. It is important that a static fluid having lower acoustic impedance than the fluid flowing within the pipe surround the sound speed meters. The advantages and effect of the vacuum backed conduit, as well as other isolation techniques, are described in commonly owned copending U.S. patent application Ser. No. 09/344,070, entitled "Measurement of Propagating Acoustic Waves in Compliant Pipes" incorporated herein by reference in its entirety.

Equation 1 can be generalized in terms of the cross-sectional area compliance ($\sigma_{conduit}$) of the conduit and the infinite sound speed and density of the fluid and the effective sound speed of the pipe/fluid system as given by:

$$\frac{1}{\rho_{eff}a_{eff}^2} = \frac{1}{\rho_{mix}a_{mix\infty}^2} + \sigma_{conduit} \quad \text{(eq 2)}$$

The cross sectional area compliance is a measure of the increase in cross-sectional area of a conduit for a given increase in internal pressure as set forth in the following relationship:

$$\sigma_{conduit} = \frac{\partial A_{cross\ section}}{\partial P} \quad \text{(eq 3)}$$

For a vacuum-backed, circular cross-section pipe of elastic modulus E, having an outside radius R, and wall thickness t, the conduit compliance is given by:

$$\sigma_{conduit} = \frac{2R}{Et} \quad \text{(eq 4)}$$

It is important to note that, in general, the cross section area compliance of the fluid/pipe system can be a complex function of frequency and amplitude and can depend on all elements acoustically coupled to the conduit. For example, if an additional fluid surrounded the conduit, the acoustic properties of the surrounding fluid would influence the cross section area compliance presented to the compressional waves propagating internal to the conduit. It is for this reason that the present invention is presented in embodiments having a vacuum backed shell surrounding the sound speed meters as described herein above.

In accordance with the present invention, using the relationships described herein above, the dependence of propagation speed of compression disturbances (one dimensional, planar compression acoustic waves) on the compliance of the conduit 12 and fluid properties (such as namely sound speed and density) can be used to determine information regarding the fluid contained within the conduit, specifically, the density of the fluid.

Referring again to FIG. 1, there is shown a density meter 1 in which the speed of sound of an unknown fluid 13 is measured within two regions $X_1$, $X_2$ wherein the pipe 12 has differing cross section area compliances associated with the two regions. A first effective speed of sound $a_{eff1}$ of the fluid/pipe system is determined from an array of pressure measurements provided by sensors of sound speed meter 14. A second speed of sound $a_{eff2}$ of the fluid/pipe system is determined from an array of pressure measurements provided by sensors of sound speed meter 16. As will be more fully described herein below, the change in propagation velocity of one dimensional acoustic waves between the two regions $X_1$, $X_2$, along with knowledge of the cross sectional compliances of each section, provides a means to determine the density of the fluid 13. As illustrated in this example, the variation in the system cross sectional compliance could be achieved through a change the conduit compliance, namely in the form of a change in wall thickness of the pipe. Other methods to vary the system cross sectional compliance are described below, and any known method of varying the system cross sectional compliance is contemplated by the present invention.

Embodiments of the present invention comprised of fiber optic based sound speed meters 14, 16 are particularly well suited for industrial sensing applications where in the installation environment is considered harsh. Such harsh environments are typically found in the industrial process area and include sensor exposure to acids, caustics, nuclear energy, electromagnetic interference and exposure to explosive vapors among other hazards. Because the sensor is glass based it is chemically impervious to most industrial process related chemicals. Further because the sensor of the present invention uses light for signal transmission it does not require any electrical power and as such is not influenced by electromagnetic fields and cannot create arcing or explosions when used in the presence of flammable vapors.

A plurality of the density meters 1 of the present invention may be connected to a common cable and multiplexed together with other sound speed meters (not shown) using any known multiplexing technique. For instance, it is contemplated that the various embodiments of the density meter 1 of the present invention include the capability of being multiplexed as well as capable of communication with various protocols and systems currently in use in the industrial sensing area. For instance, and with reference to FIG. 1 there is shown a portion of a process control incorporating a density meter 1 in accordance with the present invention with a controller 58. Signal processing logic 60 communicates density signal $\rho_x$ along line 59 to control device 70, a computer or micro-processor for example, where the information may be used to control the fluid characteristics in pipe 12 through known controls means such as a pump, valve, throttle, etc. (not shown). In certain embodiments of the control system shown and with appropriate electro-optical conversion within signal processing logic 60 of the sensor return signal to a conventional 4–20 mA signal the signal can be combined with other control devices and sensors at control device 58 via separate electrical lines. In this particular embodiment the communication from the fiber optic sensor is performed with a 4–20 mA analog signal, and the open protocol HART®. (Highway Addressable Remote Transducer) digital communications format. Similarly, communication from the fiber optic density meter 1 may also be performed with open and interoperable protocol FOUNDATION™ Field bus that provides a digital communication link among intelligent field level and control devices via electrical lines. The control device 58 can be configured for use with other process protocols, including Device Bus, Sensor Bus, Profibus, the ethernet, and others in use throughout the world. The use of fiber optic based sound speed meters make the density meter 1 of the present invention uniquely qualified for industrial applications requiring multiple sensors. The use of multiplexed density meters through the use of feedthroughs (or other known techniques) in a large multi-point process enables connectivity to the multiple density meters through a single fiber optic cable. Electronic sensors of the prior art require dedicated wiring to the sensor and back to the instrumentation. For instance, a typical industrial process control system that utilizes electronic density meters of the prior art requires an electrical process loop to facilitate both a power signal to the transmitters and bi-directional communication, and can be constructed in accordance with a number of the aforementioned process communication protocols.

In operation, industrial process uses for the present invention include reverse osmosis, coking, general refining uses, in-line pressure sensors for emissions monitoring, sensors for monitoring hydrogen, combustion control, gas composition analysis, distributed sensors in tank gauging, multiphase computational fluid dynamics, instrumentation of multiphase flows, among others.

Figure 3:
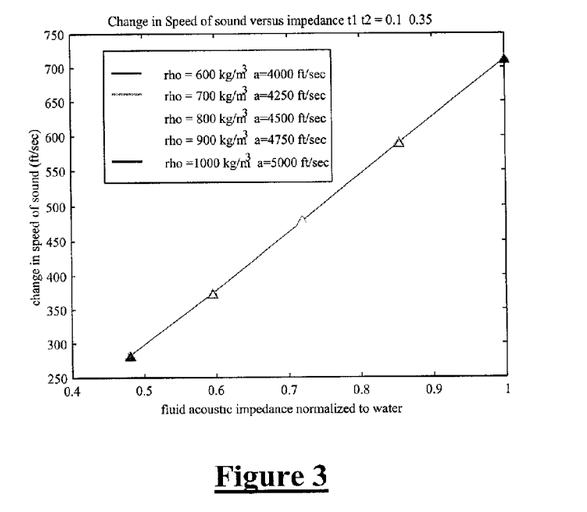
FIG. 3 is a graphical representation of the change in effective system speed of sound of a fluid/pipe for various fluid compliances, in accordance with the present invention.

The invention will now be described with attention to another specific embodiment commonly found in the oil and gas industry with reference to FIGS. 1 and 3 wherein the system cross sectional compliance is varied by varying the fluid compliance. In this exemplary embodiment the pipe 12 is comprised of a single material type, Inconel for example, have a wall thickness $t_1$ at region $X_1$ of 0.10 inches and a wall thickness of $t_2$ at region $X_2$ of 0.35 inches. The pipe is vacuum mandrel backed with a shell 15 isolating the sound speed meters from the outside environment. As best shown in FIG. 3 the change in sound speed for fluid mixtures, representative hydrocarbon and water mixtures, having densities ranging from 600 to 1000 kg/m³, is quite dramatic. As shown, the change in sound speed scales with the acoustic impedance of the fluid. For the least dense fluid with the slowest infinite medium sound speed (representing a light hydrocarbon), the change in wall thickness results in approximately 300 ft/sec change in sound speed. For the densest, highest infinite medium sound speed (representing, for example, a high watercut mixture), the change in wall thickness results in a 750 ft/sec change in sound speed. The expression for the change in effective speed of sound between two sections of vacuum-backed conduit differing only in wall thickness, where $a_o$ is the speed of sound of the fluid and $\rho_o$ is the density of the fluid is given by:

$$a_{eff_1} - a_{eff_2} = \frac{1}{\sqrt{\frac{1}{a_0^2} + \rho_o \frac{2R}{Et_1}}} - \frac{1}{\sqrt{\frac{1}{a_0^2} + \rho_o \frac{2R}{Et_2}}} \quad (eq\ 5)$$

In accordance with the present invention, the density of the unknown fluid is determined by measuring two effective system sound speeds in two regions with differing, but known structural properties. For example, in the cylindrical pipe 12 of FIG. 1 having a thickness t and elastic modulus E, the density $\rho_{mix}$ of the unknown fluid is given by:

$$\rho_{mix} = \left( \frac{1}{a_{eff_1}^2} - \frac{1}{a_{eff_2}^2} \right) \frac{E}{2R} \frac{t_1 t_2}{t_2 - t_1} \quad (eq\ 6)$$

As discussed herein above, varying wall thickness is but one way to achieve a change in system cross sectional area compliance and thereby provide a density measurement in accordance with the present invention. In general, the larger the change in system cross sectional area compliance between the two (or more regions) in which the sound speed is measured, the more robust the density measurement. In addition, an increase in the number of regions, i.e. greater than two, along a pipe with varying compliance in which system sound speeds are measured would give additional, redundant measurements of density. The additional data could yield a more robust or accurate overall system depending on the specific application.

Figure 4:
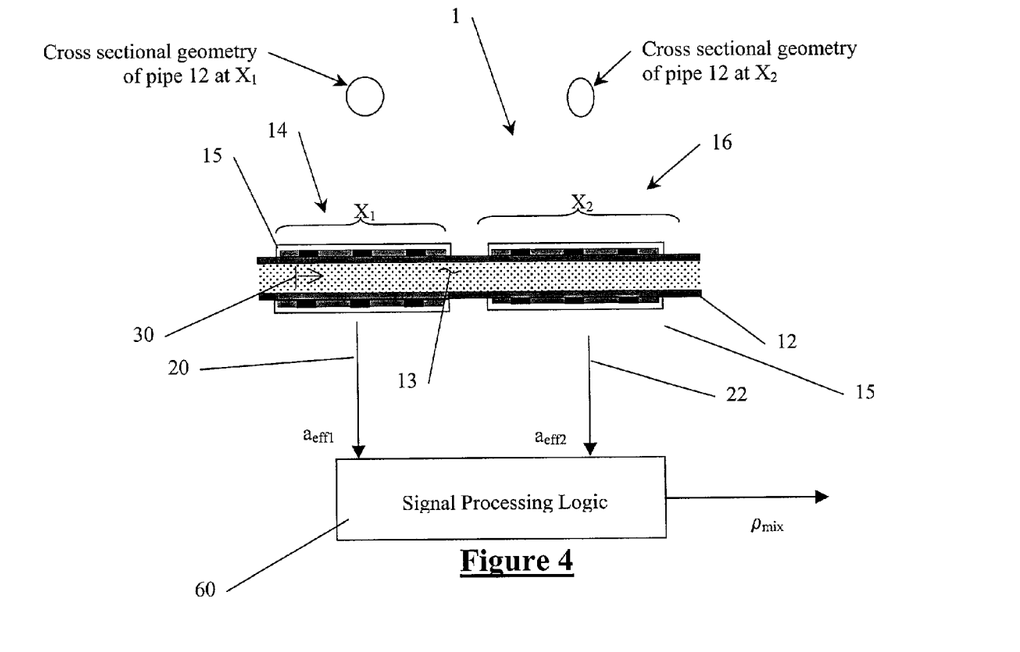
FIG. 4 is a schematic block diagram of a density meter system having an egg shaped cross section in one sensing region, in accordance with the present invention.

One alternative method to achieve large variations in system compliance by changing the conduit compliance is best shown with reference to FIG. 4 wherein a first sensing region in surrounding $X_1$ comprises a circular cross section conduit and second sensing region surrounding $X_2$ comprises a non-circular cross section conduit, shown as an egg-shaped conduit by way of example, all other properties of the pipe remaining equal. The circular geometry surrounding $X_1$ represents, for a given cross section, material modulus, and wall thickness, the configuration with the lowest cross sectional area compliance. However, the geometry of the cross section of the modified sensing region surrounding $X_2$, such as by modifying or "egging" the circular section into an oval (or other alternative shapes such as using cross section possessing flattened sides) significantly increases the compliance of the conduit 12. In certain embodiments between sensing region $X_2$ (non-circular geometry) and sensing region $X_1$ (circular geometry) of the same wall thickness t, cross sectional area compliance ratios greater than 30 are achievable. As demonstrated in the figures referenced herein above, increasing the compliance ratio of the pipe increases the sensitivity of the density meter 1 by increasing the system compliance ratio thereby increasing the change in effective system sound speed for a given fluid density.

Figure 5:
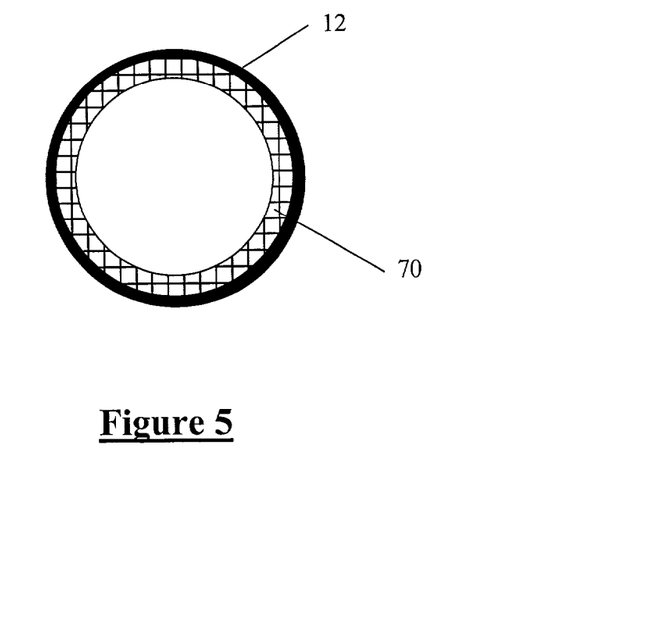
FIG. 5 is a cross sectional representation of an embodiment of a density meter having a closed cell foam liner, in accordance with the present invention.

The effective system cross sectional area compliance can be modified in a variety of manners such as, by way of example, varying materials, incorporating wall treatments, resonators or cavities. Referring to FIG. 5 there is shown a modified system cross sectional compliance technique wherein a closed cell foam 70 (or other compressible liner material) is positioned along the walls of one of the sensing sections of the pipe 12 thereby modifying the effective compliance of that section of pipe. In the embodiment shown in FIG. 5, the pipe/fluid interface would be defined as the inner surface of the liner. An increase in fluid pressure would increase the effective cross sectional area of the fluid by both compressing the foam and by expanding the pipe. It is also contemplated by the present invention that the two sensing regions may be comprised of different material types or any other variation in geometry or material property that would effectuate a difference in the compliance of the pipe between the two sensing regions.

Figure 6:
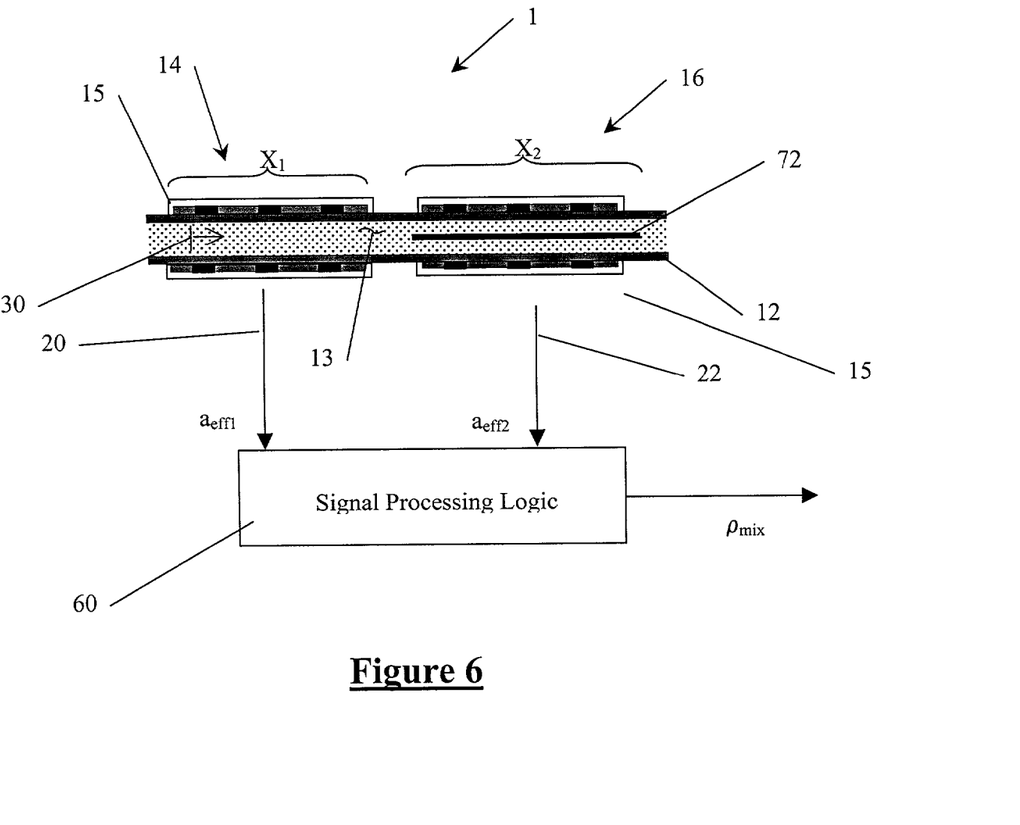
FIG. 6 is a schematic block diagram of a density meter system having a tube positioned within the flow path, in accordance with the present invention.

In another example of the present invention varying the compliance of the fluid or the area within the pipe can vary the system cross sectional compliance. For instance, referring to FIG. 6 additional system compliance could be introduced at a location along the pipe by positioning a tube 72 within the flow path along one of the sensing regions. The tube 72 would serve to modify the cross sectional compliance by compressing due to an increase in fluid pressure and would then combine with the compliance of the pipe to modify the effective sound speed of the fluid/pipe system. Other alternatives include embodiments wherein the tube is an air filled, sealed tube (or tubes) positioned within one sensing region of the pipe.

Referring again to FIG. 1 and defining α as the ratio of conduit compliance in the "soft" section, sensing region $X_1$, of the density meter 1 to that of the "stiff" section, sensing region $X_2$, of the meter, and where $\sigma_2$ is the cross sectional area compliance of sensing region $X_2$ of the meter, the density of the fluid $\rho_{mix}$ within the meter can be expressed as:

$$\rho_{mix} = \frac{1}{(\alpha - 1)\sigma_2}\left(\frac{1}{a_{eff_1}^2} - \frac{1}{a_{eff_2}^2}\right) \qquad (\text{eq 7})$$

Figure 7:
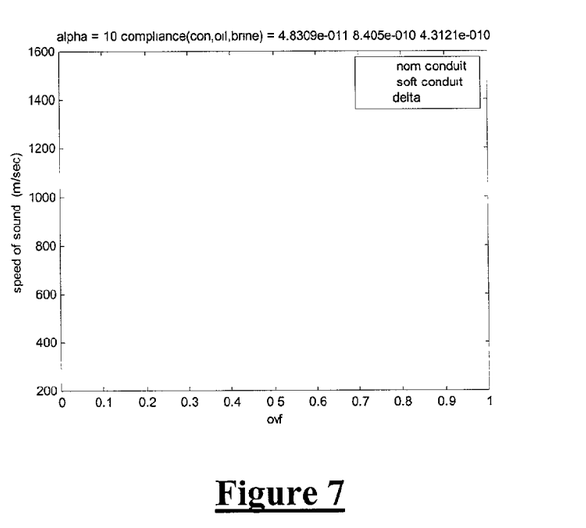
FIG. 7 is a graphical representation of the effective system speed of sound of a fluid/pipe for various volume fractions of a brine/oil mixture, in accordance with the present invention.

Referring now to FIG. 7 there is shown the speed of sound of a varying mixture of a two part brine/water fluid as measured in two sensing regions $X_1$, $X_2$, of an embodiment of density meter 1 of FIG. 1. The figure shows the various sound speeds versus oil volume fractions from 0% oil to 100% oil by volume. In the example shown the two sensing sections have a compliance ratio α of 10. As shown in FIG. 7 the difference in measured sound speed between the two sections varies from approximately 400 m/s for 100% brine, to approximately 200 m/s for 100% oil. As described herein above and depicted in the figure the effective system speed of sound as measured in the stiff section ($X_2$) is significantly higher for the mixture than that measured in the less stiff section ($X_1$) of the pipe 12.

In operation and referring again to FIG. 1, the two sound speed meters 14, 16 provide effective system sound speeds $a_{1eff}$ and $a_{2eff}$ to signal processing logic 60, which includes the relationship set forth in equation 7. The compliance of the conduit $\sigma_2$ in the second sensing region $X_2$ and the ratio of the compliances between the two sections $\sigma_1/\sigma_2$ are further provided to logic 60 to calculate the density of the mixture $\rho_{mix}$. It is an important aspect of the present invention that the density of the fluid mixture can be determined without requiring specific speed of sound and calibration information on the fluid itself. In the embodiments described thus far it is only required that the sound speed and density of the fluid itself is the same in the two section. Thus, although the density measurement described herein is based on speed of sound measurements, no knowledge of the sound speed of the fluid is required to determine density.

Figure 8:
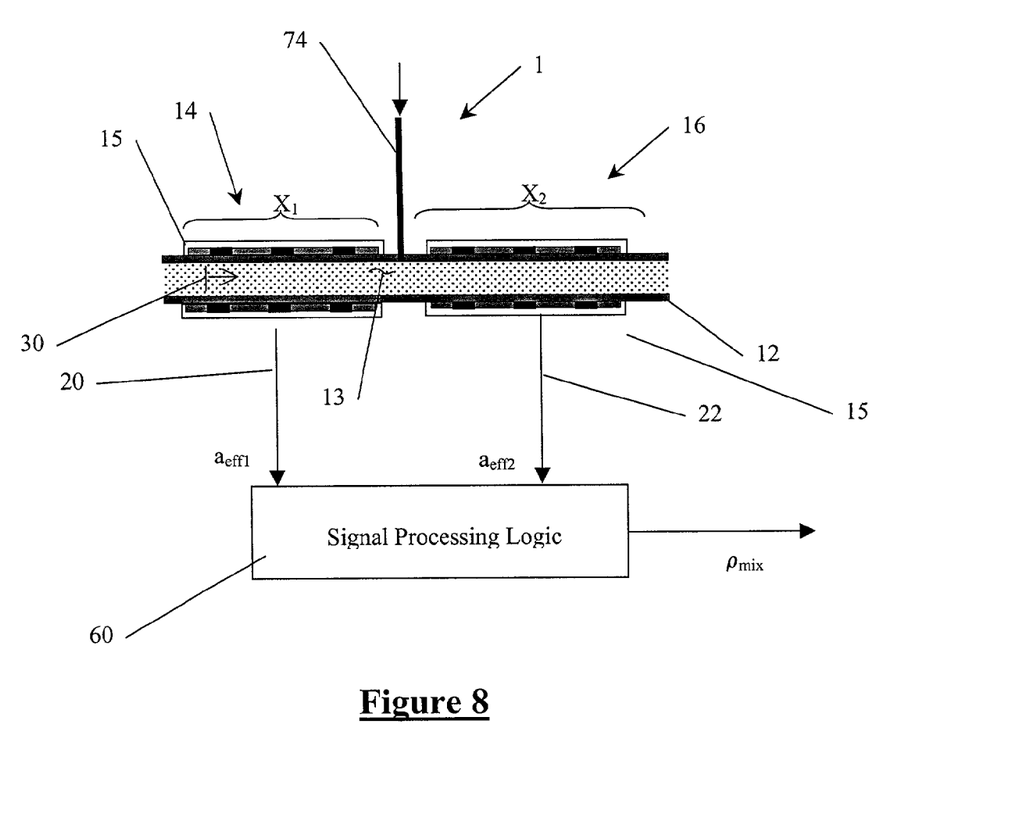
FIG. 8 is a schematic block diagram of a density meter system having an input tube positioned between the sensing regions, in accordance with the present invention.

In certain other embodiments the density of the fluid may be determined after the introduction of a known quantity of a known constituent into the fluid between the two sensing sections. Referring to FIG. 8 there is shown a density meter 1 including an input line 74 positioned between the two sensing sections $X_1$, $X_2$. In this particular embodiment the system cross sectional compliance is changed by the introduction of a constant amount of a known quantity of air 75, for example, into the fluid 13. The introduction of the air into the fluid changes the system cross-section compliance in the sensing region downstream of input line 74. The change in compliance in the fluid due to the introduction of the air is taken into account in the relationships described herein above to accurately determine the density of the fluid 13.

Figure 9:
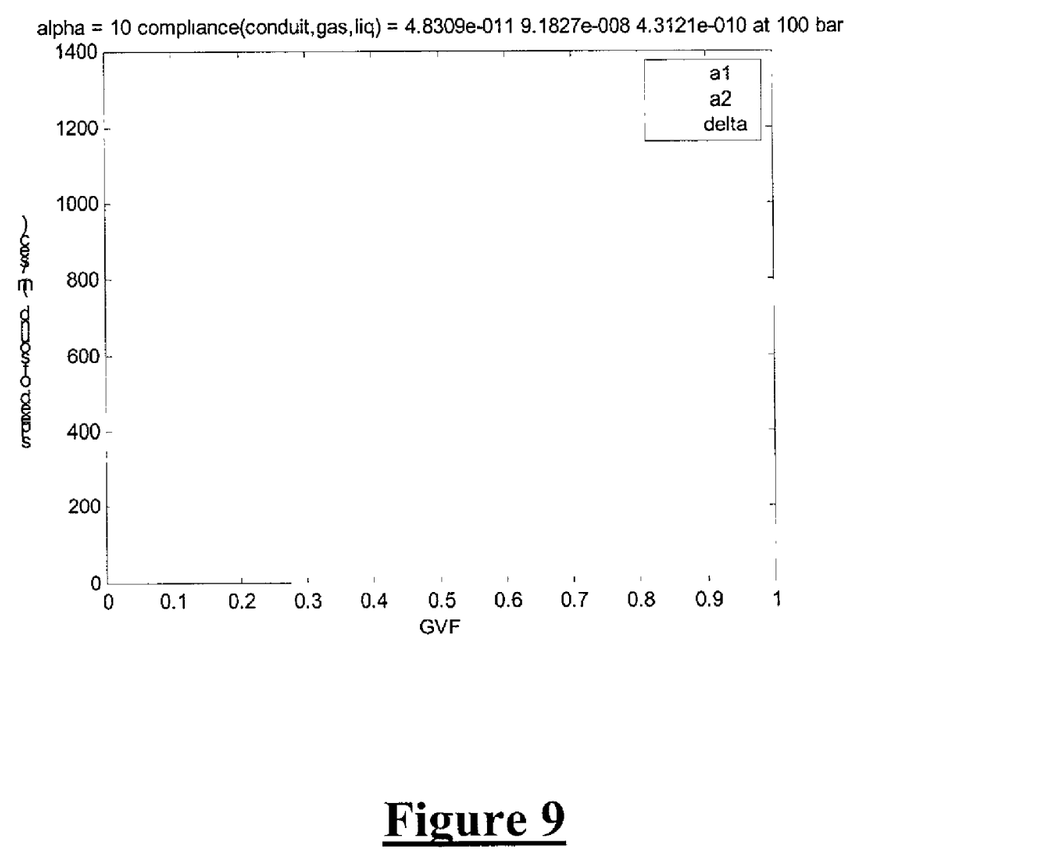
FIG. 9 is a graphical representation of the effective system speed of sound of a fluid/pipe for various volume fractions of a gas/fluid mixture, in accordance with the present invention.

In addition to liquid mixtures, the density meter of the present invention includes the ability to determine the density of gas/liquid mixtures. Referring to FIG. 9 there is shown the predicted sound speeds in the stiff ($X_2$) and soft ($X_1$) sensing regions of density meter 1 depicted in FIG. 1 for various mixtures of gas and liquids with representative single phase compliances typical of produced gases and liquids at 100 bar. As shown, due primarily to the high compliance of the gas phase at this relatively low pressure, the change in overall sound speed in the two sections of the meter due to the change in conduit compliance is much less significant for this application than those described above. From Equation 2 and defining the compliance of the fluid as the inverse of the product of the fluid density and the square of the infinite dimensional sound speed yields the following relation:

$$\sigma_{mixture} \equiv \frac{1}{\rho_{mix} a_{mix_\infty}^2} \qquad \text{(Eq. 8)}$$

and the ratio of the effective sound speed within the conduit to the infinite dimensional sound speed is given by:

$$\frac{a_{eff}}{a_{mix_\infty}} = \sqrt{\frac{1}{1 + \frac{\sigma_{conduit}}{\sigma_{mixture}}}} \qquad \text{(Eq. 9)}$$

The change in difference in sound speed for a given change in density of the fluid is a useful metric in designing the density meter described herein for any specific application. Assuming that the ratio of the cross sectional compliance introduced by the structure over that of the fluid is much less than 1, this performance metric can be expressed as follows:

$$\frac{\partial(a_{1_{eff}} - a_{2_{eff}})}{\partial \rho} = \frac{a_{mix_\infty}}{\rho_{mix}} \frac{\sigma_{Stiff}}{\sigma_{mixture}} \frac{1}{2}(\alpha - 1) \qquad \text{(Eq. 10)}$$

As shown, effectiveness of the density meter of the present invention described herein scales with both the ratio of the compliances of the two conduits as well as with the ratio of the compliance of conduit to that of the fluid. Thus, the density meter of the present invention is more effective when the system cross sectional compliance contributed by the conduit is a significant fraction of that contributed by the fluid and the ratio of the system cross sectional compliance of the two regions is significantly greater than one.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An industrial process control system for controlling at least one parameter of an industrial fluid process having at least one fluid flowing within a pipe, said system comprising:
    a density meter disposed on said pipe, said density meter comprising:
        a first sound speed meter configured to detect acoustic pressure signals the first sound speed meter positioned at a first sensing region along said pipe which provides a first effective sound speed signal, said first sensing region has a first cross-sectional compliance;
        a second sound speed meter configured to detect the acoustic pressure signals, the second sound speed meter positioned at a second sensing region along said pipe which provides a second effective sound speed signal, said second sensing region has a second cross-sectional compliance, wherein said first cross-sectional compliance is different than said second cross-sectional compliance to change the speed of sound propagating from the first sensing region to the second sensing region; and
        a signal processor, responsive to said first and said second sound speed signals, which provides a density signal indicative of said density of said fluid within said pipe; and
    a control device receiving said density signal and capable of controlling said process parameter to a predetermined level based on said density signal.

2. The industrial process control system of claim 1 wherein said pipe has a first compliance at the first sensing region and a second compliance at the second sensing region, and the first compliance and the second compliance of the pipe are different.

3. The industrial process control system of claim 1 further comprising a concentric shell positioned around each of said first and said second sound speed meters thereby isolating said first and said second sound meters from an outside environment.

4. The industrial process control system of claim 1, wherein said first and said second sound speed meters determine said first and said second sound speed signals from one-dimensional acoustic pressure waves traveling axially in said pipe.

5. The industrial process control system of claim 1 wherein said at least one of said first and said second speed meters comprises a fiber optic based sound speed meter.

6. The industrial process control system of claim 1 wherein said first or said second sensing region of said pipe comprises a non-circular cross sectional geometry.

7. The industrial process control system of claim 6 wherein said non-circular cross sectional geometry comprises an oval shape.

8. The industrial process control system of claim 1 further comprising an input line positioned between said first and said second sensing regions to provide a known quantity of a known substance into said fluid, having a fluid compliance, to change the fluid compliance.

9. An industrial process control system as set forth in claim 1 wherein said first and second sound speed meters comprise fiber optic based sound speed meters and wherein said density signal comprises a fiber optic based density signal, said process control system further comprising:
    an opto-electrical converter receiving said fiber optic based density signal and converting said fiber optic based density signal into an electrical signal indicative of said density of said fluid flowing in said pipe;
    wherein said control device receives said electrical signal and is capable of controlling said process parameter to a predetermined level based on said electrical signal.

10. The industrial process control system of claim 1, wherein at least one of the first and second sound speed meters comprises an array of at least two pressure sensors disposed axially along the pipe for measuring an acoustic pressure within the pipe, wherein the signal processor provides the corresponding first or second sound speed signal in response to the measured acoustic pressure.

11. The industrial process control system of claim 1, wherein each of the first and second sound speed meters comprises and array of at least two pressure sensors disposed axially along the pipe for measuring an acoustic pressure within the pipe, wherein the signal processor provides the corresponding first and second sound speed signal in response to the measured acoustic pressures.

12. The industrial process control system of claim 1, further includes at least one of a wall treatment, resonator and cavity disposed in at least one of the first and second sensing regions to modify at least one of the first and second cross-sectional compliances.

13. The industrial process control system of claim 1, further includes at least one liner disposed in at least one of the first and second sensing regions to modify at least one of the first and second cross-sectional compliances.

14. The industrial process control system of claim 13, wherein the liner is comprises of a compressible material.

15. The industrial process control system of claim 1, wherein first and second portions of the pipe disposed in respective first and second sensing regions is comprised of difterent geometrics to provide different first and second cross-sectional compliances.

16. The industrial process control system of claim 1, wherein first and second portions of the pipe disposed in respective first and second sensing regions is comprises of different material to provide different first and second cross-sectional compliances.

17. The industrial process control system of claim 15, wherein one of the first and second portions of the pipe disposed in respective first and second sensing regions has a nan-circular cross-section.

18. The industrial process control system of claim 1, wherein first and second portions of the pipe disposed in respective first and second sensing regions is comprised of different wall thicknesses to provide different first and second cross-sectional compliance.

19. The industrial process control system of claim 1, wherein a first portion of the pipe disposed in the first sending region has a substantially circular cross-section and a second portion of the pipe disposed in the second sensing region has a substantially non-circular cross-section.

20. The industrial process control system of claim 1, wherein the acoustic pressure signals have a frequency from about 10 Hertz to about 10,000 Hertz.

* * * * *